US005910102A

United States Patent [19]
Hastings

[11] Patent Number: 5,910,102
[45] Date of Patent: Jun. 8, 1999

[54] CONVERSION OF BETA RADIATION TO GAMMA RADIATION FOR INTRAVASCULAR RADIATION THERAPY

[75] Inventor: Roger N. Hastings, Maple Grove, Minn.

[73] Assignee: SciMed Life Systems, Inc., Maple Grove, Minn.

[21] Appl. No.: 08/781,857

[22] Filed: Jan. 10, 1997

[51] Int. Cl.[6] ................................................. A61N 5/00
[52] U.S. Cl. ............................................................. 600/3
[58] Field of Search ........................... 600/1–8; 604/158, 604/171, 280, 282, 264; 378/64–69

[56] References Cited

U.S. PATENT DOCUMENTS

| | | | |
|---|---|---|---|
| 5,059,166 | 10/1991 | Fischell et al. | 600/3 |
| 5,176,617 | 1/1993 | Fischell et al. | 600/3 |
| 5,199,939 | 4/1993 | Dake et al. | 600/3 |
| 5,213,561 | 5/1993 | Weinstein et al. | 600/7 |
| 5,302,168 | 4/1994 | Hess | 600/3 |
| 5,308,356 | 5/1994 | Blackshear, Jr. et al. | 606/194 |
| 5,354,257 | 10/1994 | Roubin et al. | 600/7 |
| 5,411,466 | 5/1995 | Hess | 600/3 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,605,530 | 2/1997 | Fischell et al. | 600/3 |
| 5,616,114 | 4/1997 | Thornton et al. | 600/3 |
| 5,618,266 | 4/1997 | Liprie | 604/21 |
| 5,674,177 | 10/1997 | Hehrlein et al. | 606/3 |
| 5,683,345 | 11/1997 | Waksman et al. | 600/3 |

FOREIGN PATENT DOCUMENTS

| | | |
|---|---|---|
| 0 433 011 B1 | 6/1991 | European Pat. Off. . |
| 0 497 495 A2 | 8/1992 | European Pat. Off. . |
| 0 593 136 A1 | 4/1994 | European Pat. Off. . |
| 0 633 041 A1 | 1/1995 | European Pat. Off. . |
| 0 688 580 A1 | 12/1995 | European Pat. Off. . |
| 9102312.2 | 6/1992 | Germany . |
| 93/04735 | 3/1993 | WIPO . |

(List continued on next page.)

OTHER PUBLICATIONS

Raloff, "Nuclear Medicine Gets Friendlier—Experimental Therapies Seek to Poison Just the Disease", *Science News*, vol. 152, Jul. 19, 1997, pp. 40–41.

Fackelmann, "Harbinger of a Heart Attack—Does a Protein in the Blood Foretell Heart Trouble", *Science News*, vol. 151, Jun. 14, 1997, pp. 374–375

"Aids and Cancer Cured by Hyper–Oxygenation", *Now What*, Issue No. 1, 1987, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulision The Question of Free Radicals", Internet Address http://www.livelinks.com/sumeria/oxy/rad2.html, Aug. 1, 1997.

Barry, "Reactive Oxygen Species in Living Systems—Source: Biochemistry, and Role in Human Disease", Internet Address http://www.livelinks.com/sumeria/oxy/reactive-.html, Jul. 21, 1997 from *American Journal of Medicine*, vol. 91, No. 3C, Sep. 30, 1991, p. 14S(9).

(List continued on next page.)

*Primary Examiner*—John P. Lacyk
*Assistant Examiner*—Samuel Gilbert
*Attorney, Agent, or Firm*—Westman, Champlin & Kelly, P.A.

[57] ABSTRACT

A method and apparatus for inhibiting restenosis of arteries utilizing Bremstralung created radiation. A preferred apparatus includes an elongate shaft having a heavy-metal envelope disposed on the distal end. The apparatus can include a second elongate shaft slidably disposed parallel to the first shaft for increasing the outer diameter of the envelope by proximally pulling the envelope distal end relative to the envelope proximal end.

18 Claims, 2 Drawing Sheets

FOREIGN PATENT DOCUMENTS

| | | |
|---|---|---|
| 94/25106 | 11/1994 | WIPO . |
| 94/26205 | 11/1994 | WIPO . |
| 95/07732 | 3/1995 | WIPO . |
| 95/19807 | 7/1995 | WIPO . |
| 95/26681 | 10/1995 | WIPO . |
| 96/06654 | 3/1996 | WIPO . |
| 96/10436 | 4/1996 | WIPO . |
| 96/13303 | 5/1996 | WIPO . |
| 96/14898 | 5/1996 | WIPO . |
| 96/17654 | 6/1996 | WIPO . |
| 96/22121 | 7/1996 | WIPO . |

OTHER PUBLICATIONS

Block, "Peroxygen Compounds, Chapter 9", *Disinfection, Sterilization, and Preservation,* Fourth Edition, Lea & Febiger, Philadelphia, Copyright 1991.

Moore, "Free Radial Generation by Thyroid Peroxidase and Its Effects on Cells in Vitro", PhD. Dissertation, Group in Endocrinology–University of California, Berkeley, California, Dec. 1990.

CONVERSION OF BETA RADIATION TO GAMMA RADIATION FOR INTRAVASCULAR RADIATION THERAPY

This application is related to U.S. patent application, Ser. No. 08/782,471, entitled "Intravascular Radiation Delivery System", filed on the same date as the present application, Roger Hastings inventor, which is a continuation-in-part of U.S. application Ser. No. 08/608,655, filed Feb. 29, 1996.

FIELD OF THE INVENTION

The invention relates generally to a method and apparatus for inhibiting restenosis in coronary arteries after angioplasty. More specifically, the invention includes dosing a vessel region with Gamma radiation initiated by a Beta emitter on an inserted catheter distal end to inhibit restenosis.

BACKGROUND OF THE INVENTION

Coronary arteries provide blood and nutrients to the heart muscle. The arteries are subject to atherosclerosis or hardening of the arteries. Vascular regions have plaques formed within, resulting in stenosed regions having reduced cross-sectional area. The reduced area causes a reduction in transport of blood, oxygen, and nutrients which can result in angina, myocardial infarction and death.

A commonly used method for treating atherosclerosis is Percutaneous Transluminal Coronary Angioplasty (PTCA). PTCA includes insertion of a balloon catheter through an insertion in the femoral artery near the groin, advancement of the balloon over the aortic arch, further advancement within the selected coronary artery, continuing until the balloon portion is placed across the stenosed region. The balloon is inflated, widening the narrowed vessel region.

After catheter withdrawal, significant vessel reclosure may develop. The reclosure may occur within hours or days of dilation, an "abrupt reclosure". When reclosure does occur, it more commonly occurs progressively, within six months of the angioplasty. The gradual reclosure is referred to as "restenosis", and largely negates the dilatation treatment.

One approach to dealing with restenosis utilizes stents, short tubular sections, placed across the recently dilatated vessel region. Stents can be either self-expanding or balloon-expandable. Stents are normally left in place indefinitely. As the stent is forever pushing radially outward against the vessel wall, the wall may be undesirably irritated over long time periods. Stent ends, which push radially outward, are adjacent to soft tissue which can be irritated by the stent end. Some believe the stent could promote restenosis in the region immediately beyond the stent ends.

Stents commonly have wire mesh or spring structures, with openings in the stent walls. "Intimal hyperplasia", rapid tissue growth through stent openings has also been reported. While the exact mechanism of restenosis is not understood, it is believed that the vessel narrowing is due more to cellular growth mechanisms than to an elastic rebound mechanism.

Thus, to prevent restenosis, use of a stent, or a stent without additional therapy may not be a solution for all patients. An alternative to stents or an additional treatment associated with the use of stents may be desirable for some patients.

One proposed alternative to standard stents is the use of radiation to inhibit restenosis using a radioactive stent. Radioactive stents are indefinitely placed devices, with the possible irritating effects of stents. Furthermore, as stents are commonly formed of open structures such as springs or meshes, portions of vessel walls near stent wires are exposed to cell killing radiation while other vessel areas more remote to stent wires are exposed to much less radiation.

SUMMARY OF THE INVENTION

The present invention includes an apparatus and method for inhibiting restenosis in blood vessels. Restenosis is inhibited by the direct application of Gamma rays and X rays to vessel walls. The invention utilizes the Bremstralung effect to produce the X rays and Gamma rays from Beta radiation source. In accordance with the Bremstralung effect, Beta radiation striking a heavy-metal such as gold or tantalum produces Gamma rays and/or X rays.

The device can include a heavy-metal envelope disposed near the distal end of an elongate shaft. One envelope construction includes gold foil or gold film longitudinal strips. A preferred device has a first, hollow shaft with a second shaft slidably disposed within. The heavy-metal envelope in this embodiment can include a distal waist and a proximal waist, with the distal end of the inner shaft attached to the envelope distal waist, and the envelope proximal waist attached to the outer shaft distal end.

The inner shaft can be withdrawn proximally relative to the outer shaft, thereby foreshortening the envelope, causing the envelope mid-region to increase in outer diameter, more closely approaching the vessel wall. A Beta emitter is inserted within the heavy-metal envelope, causing Beta radiation to strike the foil, causing Bremstralung created radiation to be emitted from the envelope. Gamma rays and/or X rays can be emitted. A preferred device for inserting a Beta source into the envelope is a point source, located near the distal region of an elongate wire. Preferred Beta sources include phosphorus 32, strontium 90, iodine 131, sulfur 35, and carbon 14. After administering the dosage, such as 15 to 30 grays delivered to the adventitia layer, the Beta source is withdrawn from the patient's body.

The present invention thus allows a recently dilatated vessel region to receive internal Gamma and X ray treatment utilizing a Beta emitter. Beta sources are generally more benign than Gamma sources, with increased ease of use and safety in handling. The immediate source of radiation is an envelope which may be in relatively close proximity to the vessel wall, presenting a source more diffuse than a point or line source of radiation. The envelope in some embodiments attains a substantially spherical shape prior to irradiation. In other embodiments, the envelope forms a substantially cylindrical shape over much of its body. The envelope can thereby be adjusted for the geometry of the region being treated. In other cases, the vessel diameter may be too large for the effective use of a focal Beta emitter, because Beta particles have a range of only a few millimeters in blood or tissue. The secondary gamma or X-rays will travel the larger distances through blood and tissue to reach the target tissues in a large vessel.

DETAILED DESCRIPTION OF THE PREFERRED EMBODIMENTS

Figure 1:
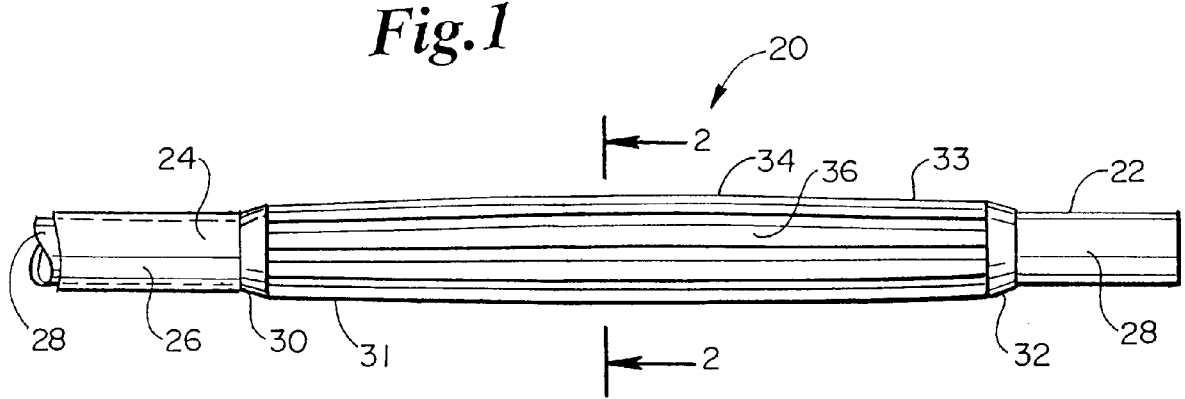
FIG. 1 is a fragmentary side view of a radiation emitting device.

FIG. 1 illustrates an intra-vascular radiation emitting catheter device 20, shown in collapsed position. Device 20 includes a distal region 22 and a less distal region 24. In the embodiment shown, device 20 has an outer shaft 26 and an inner shaft 28, shaft 28 being both parallel to and within shaft 26. A heavy-metal envelope 34 includes a plurality of longitudinal strips 36. Envelope 34 extends from a proximal waist 31 to a distal waist 33, with proximal waist 31 attached to outer shaft 26 at a proximal collar 30 and distal waist attached to inner shaft 28 at a distal collar 32. Proximal waist 31 defines generally a proximal opening into the envelope cavity.

Figure 2:
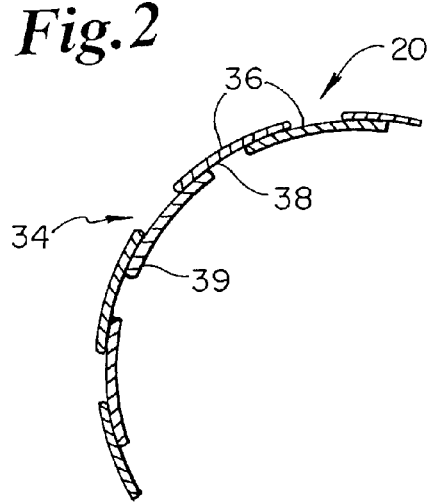
FIG. 2 is a fragmentary cross-sectional view of the heavy-metal envelope of the device depicted in FIG. 1, taken through 1—1, having overlapping longitudinal leaves.

FIG. 2 illustrates a fragmentary cross section of envelope 34, showing in more detail longitudinal strips 36 having gaps 38 therebetween and overlapping as indicated at 39. One embodiment envelope has sufficient lateral strip overlap to provide some overlap even at maximum envelope outer diameter. In a preferred embodiment, strips 36 are formed, at least in part, of gold foil. In another embodiment, strips 36 are formed of gold deposited on a substrate. In yet another embodiment, strips 36 include reinforcing fibers.

Figure 3:
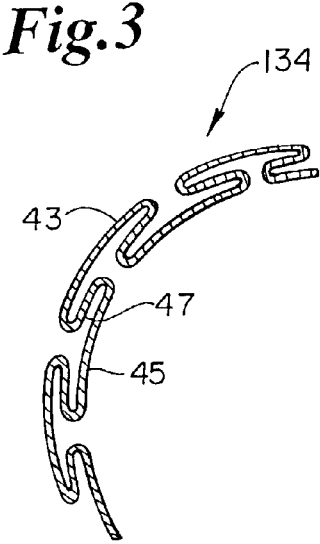
FIG. 3 is a fragmentary cross-sectional view of a heavy-metal envelope having pleats and folds.

FIG. 3 is a fragmentary cross sectional view of another embodiment 134 of the heavy metal envelope having a series of alternating outer pleats 43, folds 47, and inner pleats 45. Envelope 134 could be used in place of envelope 134 on catheter 20.

Figure 4:
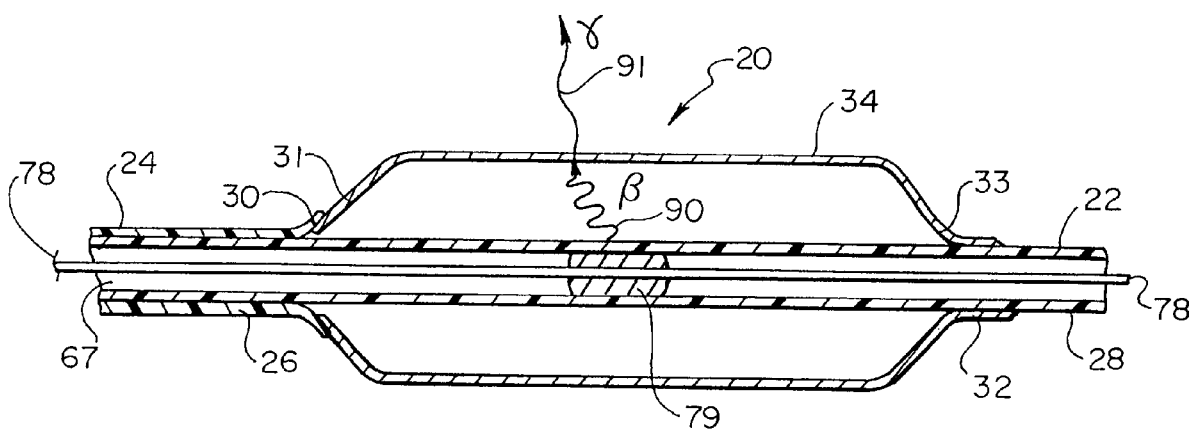
FIG. 4 is a fragmentary longitudinal cross-sectional view of a radiation emitting device in a partially expanded position.

FIG. 4 illustrates the radiation emitting catheter device 20 including an envelope 34 in a partially expanded position, having a substantially cylindrical form. The relatively long envelope form in FIG. 4 is well suited to treat longer stenosed regions. In a preferred embodiment, outer shaft 26 includes a longitudinally extending lumen. Inner shaft 28 extends through the lumen of shaft 26. In this embodiment, shaft 28 has a longitudinally extending lumen 67 through which a Beta radiation source can be advanced.

Envelope 34 is attached at distal waist 33 to inner shaft 28 at distal collar 32 and is attached near proximal waist 31 to outer shaft 26 at proximal collar 30. A Beta radiation source 79 is shown mounted on a wire 78 for insertion within device 60. Beta radiation is illustrated diagrammatically at 90, as is Gamma radiation created by the Bremstralung effect, at 91.

Figure 5:
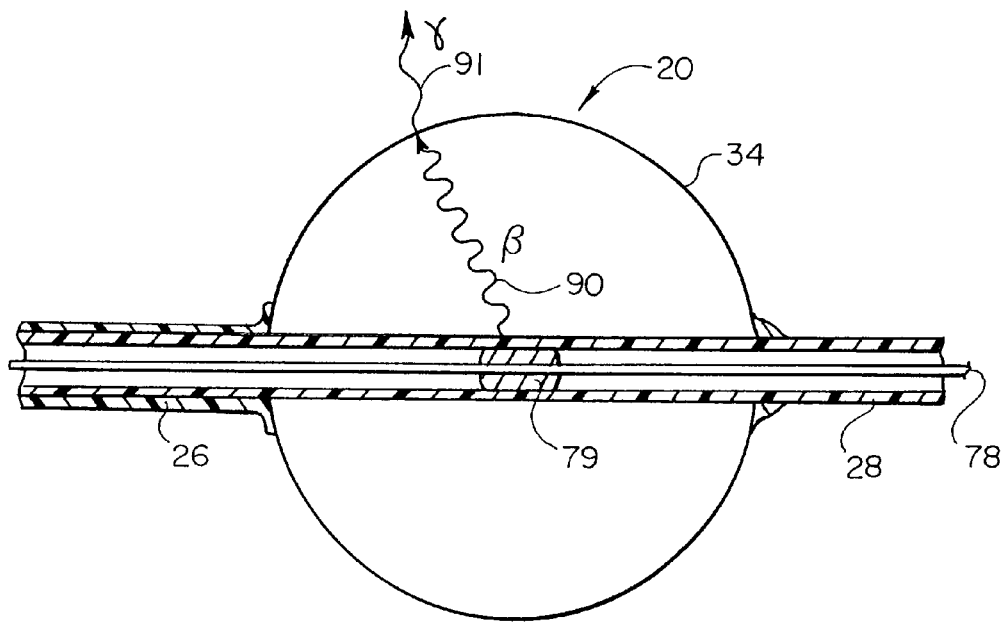
FIG. 5 is a fragmentary longitudinal cross-sectional view of a radiation emitting device in a fully expanded spherical position.

FIG. 5 illustrates radiation device 20 with envelope 34 in an extended, spherical position, resulting in a larger envelope outer diameter. The relatively shortened envelope shown in FIG. 5 is well suited for treating shorter stenosed regions. The envelope 34 is positioned for shortened and further expanded by retracting inner shaft 28 relative to outer shaft 26. Here again, Beta radiation is illustrated diagrammatically at 90 and the Gamma radiation created by the Bremstralung effect at 91.

The Bremstralung effect involves the deceleration of Beta electrons as they pass nuclei of high atomic number. The Beta particles are converted to Gamma and X ray photons. The secondary photons produced have energy which can be as high as that of the incident Beta particles. The number of secondary photons depends upon the square of the atomic number. Heavy metals including gold, lead, tantalum, and iridium produce a large number of secondary photons. The term "heavy metal" is used in the present application to refer to any material having an atomic number suitable for generating the desired Gamma and/or X rays. It is believed that gold, tantalum, tungsten, platinum, and iridium are all suitable for use as envelope material.

The envelope must be thick enough to allow the conversion of Beta particles to photons, but thin enough to allow penetration of the secondary photons. A preferred embodiment envelope is from 0.001 mm to 1 mm thick. The thickness can be varied depending on the materials chosen and the desired photon activity level. Mechanical properties may be achieved by the foil itself or by a low atomic number substrate upon which a high atomic number film is deposited.

In use, angioplasty can be performed and the angioplasty balloon catheter retracted over a guidewire, leaving the guidewire in place. A radiation emitting device according to the present invention, such as device 20 of FIG. 1 can be threaded over the guidewire and advanced to the recently dilatated region. Once in position, the guidewire can be either removed or remain in place. In a preferred method, the guidewire is removed.

With the device in place, heavy-metal envelope 34 can be adjusted, if desired, to assume the preferred geometry for the vessel and lesion to be treated. A preferred method utilizes a longer cylindrical envelope shape for longer lesions and a shorter, spherical shape for shorter lesions. A preferred apparatus for adjusting the envelope shape includes two parallel, slidably disposed shafts. In one preferred embodiment, one shaft is outer shaft 26 having the other inner shaft 28 disposed within. The envelope shape can be manipulated by drawing inner shaft 28 distally or proximally relative to outer shaft 26. Moving shaft 28 distally will foreshorten and increase the radial extent of envelope 34. By moving shaft 20 proximally, the envelope can be extended and the radial extent decreased.

An expandable envelope, having longitudinal strips as in FIG. 2, or pleats and folds in FIG. 3, provides an envelope configuration 34 or 134, respectively that can provide substantially full coverage of Beta radiation source 79 in both extended and foreshortened configuration. Beta particles emanating from within the envelope are likely to encounter a portion of the envelope, and be converted to photons, before encountering the surrounding vessel walls.

Beta radiation source 79 on wire 78, can then be advanced to the treatment site. By utilizing a Beta emitter as the primary radiation source, safe handling outside the body is possible using low density material such as plastic, for shielding. This is possible due to the low penetration of Beta particles. If a Gamma emitter were utilized as the primary radiation source, more extensive and expensive handling precautions would be necessary. When the Beta source is not within the heavy-metal envelope, Beta particles are absorbed by the patient's body and shielding the patient's body to protect medical personnel is not required. When the Beta source is within the envelope, shielding over the patient's thorax may be utilized.

As the desired distribution of radiation has been determined by setting the shape of the envelope, a Beta source having a single shape can be utilized for various treatment geometries. Specifically, a long shaped radiation source is not necessary to treat a long lesion. Specifically, controlled movements of a radiation point source over a long lesion is not necessary. As the envelope is relatively evenly distributed over the vessel inner walls relative to a point or wire source, relatively even irradiation of the vessel walls can be achieved. By generating secondary X or Gamma rays, penetration of all required tissues can be achieved even in larger peripheral arteries, due to the greater penetration and range of Gamma and X rays relative to Beta particles.

Several Beta sources including Phosphorus 32, Strontium 90, Iodine 131, Sulfur 35, and Carbon 14 are believed to be suitable for the present invention. Dosage will be determined by the treating physician. A dosage believed to be effective is about 15 to about 30 gray delivered to the tunic adventitia layer of the vessel.

The catheter of FIGS. 1, 4 and 5, may in addition contain a centering means surrounding the heavy metal foil enclosure 34. This centering means keeps the Beta source and metal enclosure centered in the artery to avoid over/under exposure to the arterial wall. It can consist of an inflatable balloon structure, and can allow perfusion of blood therethrough. A suitable centering device is disclosed in U.S. patent application Ser. No. 08/782,471, entitled "Intravascular Radiation Delivery System", invented by Roger Hastings, filed the same day as the present application and incorporated herein by reference.

With the proper dose delivered, the Beta source can be retracted from the envelope and the patient. The envelope may then be collapsed into a smaller outer diameter and retracted from the patient. With the stenosed region irradiated, restenosis should be inhibited.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. An elongate intra-vascular device for emitting radiation comprising:
    a first elongate shaft member having a distal region;
    a heavy-metal envelope attached to said first shaft distal region and a Beta radiation source within said envelope.

2. A device as recited in claim 1, wherein said envelope has an interior cavity, wherein said first elongate shaft includes a first lumen having an opening in said distal region, said opening being in communication with said envelope interior cavity.

3. A device as recited in claim 2, wherein said envelope has an outer diameter, further comprising means for increasing said envelope outer diameter.

4. A device as recited in claim 3, wherein said envelope has a proximal portion and a distal portion, wherein said means for increasing said envelope outer diameter includes a second elongate shaft having a distal region, said second elongate shaft slidably disposed parallel to said first elongate shaft, said envelope proximal portion being attached to said first shaft distal region, and said envelope distal portion being attached to said second shaft distal region.

5. A device as recited in claim 4, wherein said second shaft is slidably disposed within said first shaft.

6. A device as recited in claim 5, wherein said envelope includes a plurality of longitudinal strips.

7. A device as recited in claim 6, wherein said strips have laterally overlapping regions.

8. A device as recited in claim 6, wherein said heavy-metal includes gold and said strips include material selected from the group consisting of gold foil and gold film.

9. A device as recited in claim 6, further comprising means for centering said Beta radiation source.

10. A device as recited in claim 9, further comprising means for perfusing blood through said radiation emitting device distal region.

11. A device as recited in claim 1, wherein said heavy-metal is selected from the group consisting of gold, tantalum, tungsten, platinum and iridium.

12. An elongate intra-vascular radiation emitting assembly having a distal region comprising:
    a first elongate shaft member having a distal region;
    a heavy-metal envelope attached to said first shaft distal region for disposing a Beta radiation source within; and
    a Beta radiation source disposed within said envelope.

13. A method for inhibiting restenosis at a site comprising the steps:
    providing an elongate intra-vascular radiation emitting device having a distal region including a first elongate shaft having a distal region and a heavy-metal envelope attached to said first shaft distal region for disposing a Beta radiation source within;
    providing a Beta radiation source;
    advancing said radiation device distal region to said site;
    inserting said Beta radiation source within said envelope;
    causing said envelope to emit Bremstralung created radiation near said site.

14. A method as recited in claim 13, wherein said heavy-metal is selected from the group consisting of gold, tantalum, tungsten, platinum and iridium.

15. A method as recited in claim 13, wherein said Beta source is selected from the group of Beta emitters consisting of phosphorus 32, strontium 90, iodine 131, sulfur 35, and carbon 14.

16. A method as recited in claim 13, wherein said emitted Bremstralung created radiation is delivered to the tunic adventitia vessel layer in a dose ranging from about 15 to about 30 grays.

17. A method as recited in claim 13, wherein said emitted Bremstralung created radiation includes Gamma rays.

18. A method as recited in claim 13, wherein said emitted Bremstralung created radiation includes X rays.

* * * * *